United States Patent
Patel

(10) Patent No.: US 10,537,507 B2
(45) Date of Patent: Jan. 21, 2020

(54) ALL-IN-ONE SKIN BRIGHTENING FORMULATIONS SPECIFICALLY FOR PREGNANT SUBJECTS

(71) Applicant: Purvisha Patel, Memphis, TN (US)

(72) Inventor: Purvisha Patel, Memphis, TN (US)

( * ) Notice: Subject to any disclaimer, the term of this patent is extended or adjusted under 35 U.S.C. 154(b) by 0 days.

(21) Appl. No.: 16/526,782

(22) Filed: Jul. 30, 2019

(65) Prior Publication Data

US 2019/0350828 A1 Nov. 21, 2019

Related U.S. Application Data

(62) Division of application No. 15/143,115, filed on Apr. 29, 2016, now Pat. No. 10,363,207.

(51) Int. Cl.

| | |
|---|---|
| *A61K 8/365* | (2006.01) |
| *A61K 8/9789* | (2017.01) |
| *A61K 8/67* | (2006.01) |
| *A61K 8/34* | (2006.01) |
| *A61K 8/64* | (2006.01) |
| *A61Q 19/02* | (2006.01) |
| *A61K 8/11* | (2006.01) |
| *A61K 8/73* | (2006.01) |
| *A61K 8/49* | (2006.01) |

(52) U.S. Cl.
CPC ............. *A61K 8/365* (2013.01); *A61K 8/11* (2013.01); *A61K 8/347* (2013.01); *A61K 8/498* (2013.01); *A61K 8/64* (2013.01); *A61K 8/671* (2013.01); *A61K 8/675* (2013.01); *A61K 8/678* (2013.01); *A61K 8/735* (2013.01); *A61K 8/9789* (2017.08); *A61Q 19/02* (2013.01); *A61K 2800/5922* (2013.01)

(58) Field of Classification Search
None
See application file for complete search history.

(56) References Cited

FOREIGN PATENT DOCUMENTS

WO WO-2007051596 A1 * 5/2007 .......... C07D 495/04

* cited by examiner

*Primary Examiner* — Jessica Worsham
(74) *Attorney, Agent, or Firm* — William S. Parks

(57) ABSTRACT

Certain dermatological formulations for direct skin application that correct for hyperpigmentation effects are provided. Such formulations include a number of different compounds that work synergistically to effectuate multiple and varied pathways to pigment removal and/or brightening within the dermal layer. The ability to do so without the necessity for hydroquinone, and thus with a suitable composition that is safe for handling and utilization by pregnant and nursing women, is accorded through a combination of specific ingredients in limited proportional ranges, as well. Such ingredients include kojic acid, niacinamide, sodium hyaluronate, tocopherol, and licorice extract in very narrow ranges proportionally within an aqueous serum. The method of manufacture and use thereof such formulations are encompassed within the invention as well.

8 Claims, No Drawings

ALL-IN-ONE SKIN BRIGHTENING FORMULATIONS SPECIFICALLY FOR PREGNANT SUBJECTS

CROSS-REFERENCE TO RELATED APPLICATION

This application is a divisional application of and claims priority to co-pending U.S. patent application Ser. No. 15/143,115, filed on Apr. 29, 2016, the entirety of which is hereby incorporated by reference.

FIELD OF THE INVENTION

The present invention relates to certain dermatological formulations for direct skin application that correct for hyperpigmentation effects. Such formulations include a number of different compounds that work synergistically to effectuate multiple and varied pathways to pigment removal and/or brightening within the epidermis. The ability to do so without the necessity for hydroquinone, and thus with a non-irritating complex that is also suitable for handling and application by pregnant and nursing women, is accorded through a combination of specific ingredients in limited proportional ranges, as well. Such ingredients include kojic acid, niacinamide, sodium hyaluraonate, tocopherol, and licorice extract, in very narrow ranges proportionally within an aqueous serum. The method of manufacture and use thereof such formulations are encompassed within the invention as well.

BACKGROUND OF THE INVENTION

Melanin is the primary cause of skin colorations in mammals, particularly humans. Broadly speaking, this pigment provides a number of beneficial characteristics to humans, most notably, perhaps, the ability to protect from Ultraviolet-B (UV-B) radiation (commonly associated with exposure to sun rays or in tanning beds). Such a compound is naturally produced within the skin, through melanogenesis within melanocytes at the base of the epidermis. The amino acid tyrosine is the base source of such a pigment (as well as a number of other important compounds within the body, including adrenaline), reacting with tyrosinase to initially form Dopa and Dopaquinone. This converted base compound then either reacts with cysteine to form pheomelanins, which contribute to pink and red colorations within a person's hair and skin, or converts further to leucodopachrome and ultimately to a generally accepted polymer of 5,6-dihydroxyindole (or like structures) to form eumelanins, the dark-colored pigments that are most prevalent within skin and hair. These reactions ultimately occur in relation to melanosomes present in the epidermis of the skin and are transferred via dendritic formations from the melanocytes themselves to keratinocytes located within the outer skin layers (as well as the hair follicles and hairs, too). Although the complexities of such melanin compound formation are far more in-depth than summarized above, such pathways are typically and generally understood as the basis of such pigment generation via natural routes.

As important as such pigments are to human development and skin protection, the potential for uncontrolled melanin generation and transfer to keratinocytes, particularly in localized and/or clustered areas of a person's skin, has proven to cause certain undesirable and potentially harmful effects. For instance, hyperpigmentation of the skin has proven to be problematic on a number of levels, dependent largely upon the individual involved. For instance, uneven skin tone and localized dark coloration blemishes contribute to cosmetic difficulties. Likewise, other troubling conditions associated with hyperpigmentation may occur, including Celiac Disease, Grave's Disease, and Addison's Disease, to name but a few. In essence, the overabundance of melanin build up within concentrated skin regions is undesirable and potentially harmful to humans, necessitating investigations into possible remedies that allow for safe and reliable skin brightening/lightening effects.

Generally, however, such treatments for hyperpigmentation have proven rather elusive, at least in terms of effectiveness and overall acceptance for safety. As noted above, such a dark pigment is derived through some rather complicated in situ reactions from the amino acid Tyrosine. The ability to control such a reaction, particularly in terms of final melanin synthesis, has thus led to centered developments at certain points in the pigment creation pathway. Most notably is the initial conversion of Tyrosine to Dopa and then Dopaquinone. Again, as alluded to above, Tyrosinase is required to convert the initial Tyrosine amino acid to Dopa, as well as the further conversion thereof to Dopaquinone. As such, many skin brightening compositions and methods solely concern the deactivation or otherwise reduction of efficacy of such an enzyme in order to prevent such conversions in the first place. The problems with these past attempts at skin brightening through this limited method are primarily the reliance upon individual compounds that function to reduce Tyrosinase generation, presence, and/or activity to attain such a result. The most common individual compounds utilized for this purpose have been hydroquinone, kojic acid, and arbutin. Hydroquinone, unfortunately, has been considered a potential carcinogen, particularly in large doses (e.g., greater than 5% by weight of an applied formulation), as well as a skin irritant that creates more problems than it solves (particularly in terms of cytotoxicity). This compound also exhibits a significant rate of oxidation upon exposure to the environment (air and light, for instance), thus lowering efficacy, not to mention upon exposure to Tyrosinase itself (thus requiring exactness in terms of actual proportions present to accord any degree of effectiveness at deactivating the enzyme). Arbutin is a glycosylated hydroquinone that exhibits similar effects as hydroquinone itself, and is particularly susceptible to reactions that remove the glycoside function on the base compound, thus rendering the same basic compound known for carcinogenicity. Kojic acid, on its own, is rather limited in its effects with Tyrosinase activity, particularly due to low bioavailability and resultant low efficacy.

In any event, the ability to inhibit production of Tyrosinase within the body (or, again, causing deactivation thereof within the body) may allow for melanin production at a reduced rate. Skin brightening is thus possible through the inclusion of acceptable levels of such Tyrosinase inhibitors within skin application formulations. Coupled with a compound (or compounds) that aids in removing epidermal layers (particularly if the most trouble melanin production locations are in those layers), the potential to effectuate melanin-containing epidermis layer removal and simultaneous prevention of further melanin production may result in favorable results in this manner. Again, however, the main deficiencies of the formulations currently available for such a purpose are the utilization of hydroquinone as typical main ingredient, and the lack of a suitable epidermis removal compound that does not protect from the irritating effects of the hydroquinone compound on and within such exposed epidermis layers.

There thus remains a need for an acceptable and effective method of providing melanin removal from dermal layers and/or reduction in melanin production capability within the body itself. Such a method and formulation would preferably utilize more than just tyrosinase inhibition as the means for such an end result, primarily due to the necessity for undesirable amounts of suspect and/or ineffective compounds to that end. As well, the utilization of retinol or like product on its own for skin layer removal purposes is frowned upon due to long-term harmful effects associated with such an action and potential scarring results as well. Thus, the introduction and undertaking of other pathways in addition to those noted above would be of significant interest, particularly if the results provided not only the beneficial melanin reduction, etc., within a target patient's skin layers, but also other results such as skin scar repair and softening, at least. The ability to impart such effects with formulations that are not only free from known carcinogens, but also free from compounds that may be potentially harmful to pregnant and/or nursing women (since significant and unwanted melanin colorations are associated with pregnancy and childbirth), would be a noticeable and invited improvement in this art as well. To date, however, such a new development in this area has yet to be provided.

ADVANTAGES AND SUMMARY OF THE INVENTION

It is an advantage of the present invention to provide a safe and reliable all-in-one skin treatment formulation to provide skin brightening, improve skin texture, prevent and/or remove skin scarring, and to alleviate any hyperpigmentation problems. It is an additional advantage of the invention to provide such a formulation that is storage-stable and has a significant shelf-life. Yet another advantage is the ability to provide such effects for pregnant skin patients without any appreciable deleterious effects.

Accordingly, the invention encompasses an all-in-one skin treatment formulation comprising a base composition of ingredients of:
 from 91.78 to 96% by weight of water;
 from 0.0001 to 2% by weight of Kojic Acid;
 from 0.05 to 0.15% by weight of Niacinamide;
 from 0.8 to 1.2% by weight of Sodium Hyaluronate;
 from 0.008 to 0.012% by weight of Licorice Extract; and
 from 0.08 to 0.012% by weight of Tocopherol;
 and, as further components, from 0 to 5% by weight of a biomimetic encapsulated whitening peptide,
 from 0 to 0.01% by weight of Retinol,
 from 0 to 1.1% by weight of preservatives, such as, without limitation, phenoxyethanol, azealic acid, malic acid, and salicyclic acid,
 from 0 to 2.5% of lactic acid,
 from 0 to 2.5% of glycolic acid, and
 from 0 to 2% by weight of Hydroquinone.

Further, more specific, formulations providing synergistic effects for such an all-in-one result (in other words, the ability to provide such results without the need for multiple treatments of different compositions to the same patient's skin area) are provided and discussed in greater detail below. The particular formulations involved though, as noted above, include a base collection of ingredients, notably the aqueous solvent (whether tap or deionized water), Kojic acid, Niacinamide, Sodium hyaluronate, Licorice Extract, and Tocopherol. Each of these constituents are present within certain ranges, or, again, as noted in greater detail below, in specific amounts, to provide the synergistic reactions that accord the desired skin brightening, scar removal, etc., effects in the singular treatment. In particular, Kojic acid is known as a fungal metabolic product in certain forms, including, without limitation, as monoesters and diesters of the base acid. Niacinamide is better known, perhaps, as a variation of Vitamin B3. Licorice extract is typically provided from licorice root (*Glycyrhizza glabran*) and preserved in glycerin, water, and possibly phenoxyethanol. Sodium hyaluronate is a glycosaminoglycan structure that provides certain wrinkle-reduction properties. Tocopherol is a general term attributed to a family of compounds, more commonly referred to as tocotrienols. These compounds may include different stereoisomers of the basic structure, namely alpha-, beta-, gamma-, and even delta-tocopherol. As well, these compounds may be esterified, providing, as merely one example, tocopherol-acetates, for inclusion as an antioxidant composition within larger formulations. As it concerns the present invention, these components within the base composition of the main formulation are known, at least to a certain degree, to provide some levels of skin treatments. In combination, however, these base components have not been disclosed or formulated for any such purpose, nor have any synergistic possibilities been explored to such an end, either.

As it is, however, these base components are just that, base constituents within larger formulations, dependent on the subject patient to which such formulations are directed. Hydroquinone, for example, is generally avoided as a skin treatment component and is now prohibited for direct skin contact in amounts above 2% by weight. Such a compound, however, is highly effective at removing hyperpigmentation from certain individuals' skin, albeit with underlying suspect end results if undertaken improperly. As it is, though, the utilization of hydroquinone is desired in certain situations, with the unfortunate limitation at this point that low amounts are now permitted for such a purpose. Thus, it is understood that topical formulations including such low amounts of hydroquinone are less effective in this manner than others in the past. The utilization of the base composition, noted above, in combination with hydroquinone, for certain subject patients, at least, has been found to provide highly effective skin brightening results without resorting to multiple formulation treatments, but a single repetitive application of the same overall composition. These results are on par with high levels of hydroquinone, but without the necessity of such suspect amounts thereof. When hydroquinone is included with the base composition, then, the amount of Kojic Acid needed is actually reduced significantly (to 0.0001% by weight, for instance), ostensibly because the hydroquinone most likely dominates the effects of Kojic Acid in such a situation), retinol (a variation of Vitamin A that is effective at removing dead skin cells and facilitating the growth of new skin cells) is also included (about 0.01% by weight), and a preservative, such as phenoxyethanol (about 1% by weight, for example), is introduced, as well. Such a formulation in this manner is provided for patients that have significant hyperpigmentation and, at least to some degree, visible scarring in relation to sun-related exposure. The inclusion of hydroquinone, however, if not retinol, militates against utilization with pregnant subject patients.

Pregnant subjects may utilize, however, the same base composition, again, as outlined above, but with a Kojic Acid level at about 1% by weight, the presence of glycol and lactic acids as solvents with water (about 5% by weight of the acids and 92% or so of the water), and malic, azealic, and salicyclic acids in very low amounts (roughly 0.0003% by weight in total) as preservatives. Such an overall formulation is, as before, highly effective in its synergistic activity to provide a single (all-in-one) formulation for repeated applications on affected skin areas for a pregnant subject patient. The ability to reduce hyperpigmentation with the other benefits (scarring removal/reduction, etc.) is further accorded the user in such a situation, but without the potential (and/or prohibited) contact with chemicals that may prove harmful to a fetus in utero.

Another potential type of formulation also avoids the inclusion of hydroquinone, with replacement through a larger amount of Kojic Acid (about 2% by weight, for instance), and a substitute component that accords effective whitening to skin without suspect carcinogenic potentials. One type of component in this manner is known as Beta-White™ (Lucas Meyer Cosmetics), and is described as a biomimetic encapsulated whitening peptide. In greater detail, this component is a combination of water, butylene glycol, hydrogenated lecithin, sodium oleate, oligopeptide-68, and sodium ethylene diamine-tetraacetic acid (EDTA). Such a component has been utilized on its own in formulations as the sole skin brightening constituent; in this inventive formulation, it has been introduced and provides a synergistic effect that allows for the single application effects highly desired and prized within the industry. When introduced with the base composition, the water level is roughly 92% by weight and retinol is also present in an amount of about 0.01% by weight, as well.

Although three types of formulations are noted above including the base composition, as defined above, as well, it should be well understood by the ordinarily skilled artisan that any number of combinations may be undertaken that fall within the confines of the ranges disclosed that will accord the desired all-in-one results (and thus the synergistic benefits thereof). In other words, it is believed, without resorting to any definitive scientific conclusions, that the single formulation applications described herein provide reductions to pathways toward skin pigmentation, both facultative and constitutive in nature. As noted, standard types in the past utilized multiple formulations to skin areas, or were limited to higher amounts of suspect ingredients to achieve the desired skin brightening results. In this situation, it was realized that certain ranges of proportions of base components coupled with certain solvents, substitute brightening agents, and preservatives, at least, synergistically, and thus surprisingly, allowed for single formulation applications (though potentially repetitive over certain timeframes) to accord the necessary and desired skin brightening, low scarring, etc., improvements. To date, then, these single formulations have not been provided within the industry, and certainly not in terms of providing different directed treatments for different types of patients (again, pregnant women are in a classification that should avoid certain suspect chemicals, but, of course, would be desirous of a single, all-in-one formulation to help with skin pigmentation concerns). The utilization of such a specific type of all-in-one formulation may also be combined with sunscreen treatments, whether together or separately from the all-in-one skin brightening, etc., formulation, as well, and if desired.

The all-in-one formulations, being mainly aqueous-based in nature, are generally provided as a viscous serum and/or liquid, that applies to remains on the subject patient's skin upon application thereto. The user may apply the serum formulation and rub it into the skin, if desired, or apply with a sponge, or like implement, as well. The all-in-one formulation is typically provided in a storage-safe container with a snap- or screw-on top and with a dispensing component that allows for dosaging through squeezing the bottle itself (at least to a certain degree). The storage container may also include a pump dispenser, if desired, for dosaging the serum on demand, as well. The storage container may also provide a light-protective layer to reduce the propensity of degradation of the constituent components during storage, if desired.

The formulation may be processed and manufactured in different ways. One potentially preferred method would be to initially heat the selected amount of water to about 80° C., allow it to then cool to 35° C., then add each ingredient and mix such constituents therein until well dispersed and uniform in overall appearance, then to add such a blend to a batch at the necessary (or otherwise desired) proportions. The final batch, at the necessary percentages of all components, may then be introduced within different storage (sales) containers, packaged, distributed, and then sold to retail establishments and/or end users. If the hydroquinone formulation is desired, the manufacturing method would more appropriately include the omission of the hydroquinone initially and mixing the other constituents into a thin, uniform slurry, at which point the slurry is provided within a batch and the hydroquinone is further introduced therein.

These skin brightening, skin scarring reducing, etc., all-in-one formulations may be provided as stand-alone skin treatments, certainly. Additionally, if desired, such formulations may be further introduced within other types of personal care compositions, including, without limitation, skin softeners, antiperspirants, deodorants, cosmetics, body sprays, body washes, skin conditioners, sunscreens, make-up foundations, and the like.

DESCRIPTION OF THE PREFERRED EMBODIMENTS

The following examples are not intended to provide any limitation to the scope and bounds of the disclosure herein. The blends were made in accordance with the batch methods described above.

Formulations

Example 1

| Chemical Brightening Complex Blend with Hydroquinone | |
|---|---|
| Ingredient (*indicates base composition component) | % (by weight) |
| Water* | 95.78 |
| Kojic Acid* | 0.0001 |
| Niacinamide* | 0.10 |
| Sodium Hyaluronate* | 1.00 |
| Licorice Extract* | 0.01 |
| Tocopherol* | 0.10 |
| Hydroquinone | 2.00 |
| Retinol | 0.01 |
| Phenoxyethanol | 1.00 |

Example 2

| Brightening Complex Blend with Beta-White | |
|---|---|
| Ingredient (*indicates base composition component) | % (by weight) |
| Water* | 92.78 |
| Kojic Acid* | 2.00 |
| Niacinamide* | 0.10 |
| Sodium Hyaluronate* | 1.00 |
| Licorice Extract* | 0.01 |
| Tocopherol* | 0.10 |
| Beta-White ™ | 5.00 |
| Retinol | 0.01 |

Example 3

| Brightening Complex for Pregnant Patients | |
|---|---|
| Ingredient (*indicates base composition component) | % (by weight) |
| Water* | ~92.78 |
| Kojic Acid* | 1.00 |
| Niacinamide* | 0.10 |
| Sodium Hyaluronate* | 1.00 |
| Licorice Extract* | 0.01 |
| Tocopherol* | 0.10 |
| Glycolic Acid | 2.50 |
| Lactic Acid | 2.50 |
| Malic Acid | 0.0001 |
| Azealic Acid | 0.0001 |
| Salicyclic Acid | 0.0001 |

Testing Protocols

Each formulation above was then introduced within a batch composition to dilute to a suitable concentration for a resultant serum and then tested on individual subjects. Each human female test subject was treated with an application of roughly 5 mL of the resultant serum on a specific skin area exhibiting hyperpigmentation. The application was made daily for 6 consecutive weeks, with review of the treated skin areas each week. The case studies employed were thus non-randomized but controlled, and each subject was further treated in combination with a film of sunscreen (SPF 30) each morning of the six-week period. Three subjects were used for each formulation provided above, thus resulting in 9 patient subjects for testing purposes. Each subject exhibited improved results subsequent to the treatment period. All but 1 subject patient exhibited improvements during the six-week period of improved skin texture, improved fine lines within the treated skin area, and reduced hyperpigmentation. Such a subject, however, had excessive sun exposure in the skin area affected and photoprotection was minimal in that area as a result. Again, subsequent to the full treatment period, that single subject also exhibited improvements in all areas, such "problems" were solely during the treatment period itself. The subjects all exhibited fading of any post inflammatory pigmentation and reduced appearance of any scarring within the treated skin areas as well. Effectively, then, this all-in-one formulation, whether with regard to any of the types noted above, provided workable, safe, and reliable skin brightening results for all subject patients.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

What I claim is:

1. An all-in-one skin treatment formulation comprising a base composition of ingredients of:
   from 91.78 to 96% by weight of water;
   from 0.0001 to 2% by weight of Kojic Acid;
   from 0.05 to 0.15% by weight of Niacinamide;
   from 0.8 to 1.2% by weight of Sodium Hyaluronate;
   from 0.008 to 0.012% by weight of Licorice Extract; and
   from 0.08 to 0.12% by weight of Tocopherol;
   at most 2.5% of lactic acid, wherein at least some lactic acid is present;
   at most 2.5% of glycolic acid, wherein at least some glycolic acid is present; and
   at most 0.0003% by weight of preservatives, wherein at least some preservatives are present;
   wherein said base formulation is free from hydroquinone and retinol.

2. The formulation of claim 1 wherein said preservatives are selected from the group consisting of malic acid, azelaic, acid, and salicylic acid.

3. The formulation of claim 2 wherein all of said preservatives are present in an amount of 0.0001% by weight each.

4. The formulation of claim 1 wherein said formulation includes the ingredients of:
   Kojic Acid 1.00
   Niacinamide 0.10
   Sodium Hyaluronate 1.00
   Licorice Extract 0.01
   Tocopherol 0.10
   Glycolic Acid 2.50
   Lactic Acid 2.50
   Malic Acid 0.0001
   Azealic Acid 0.0001
   Salicyclic Acid 0.0001
   and the balance water, wherein each measure is % by weight of the entire formulation.

5. A method of providing a skin brightening effect to an area of human skin exhibiting hyperpigmentation, said method comprising the steps of:
   a) providing the formulation of claim 1; and
   b) applying said formulation to said area of human skin.

6. A method of providing a skin brightening effect to an area of human skin exhibiting hyperpigmentation, said method comprising the steps of:
   providing the formulation of claim 2; and
   b) applying said formulation to said area of human skin.

7. A method of providing a skin brightening effect to an area of human skin exhibiting hyperpigmentation, said method comprising the steps of:
   a) providing the formulation of claim 3; and
   b) applying said formulation to said area of human skin.

8. A method of providing a skin brightening effect to an area of human skin exhibiting hyperpigmentation, said method comprising the steps of:
   a) providing the formulation of claim 4; and
   b) applying said formulation to said area of human skin.

* * * * *